United States Patent [19]
Dogre Cuevas

[11] Patent Number: 5,938,619
[45] Date of Patent: Aug. 17, 1999

[54] INFANT EXTERNAL TEMPERATURE MONITORING TRANSMITTER APPARATUS WITH REMOTELY POSITIONABLE RECEIVER ALARM MECHANISM

[76] Inventor: Miguel E. Dogre Cuevas, 3840 Harding Ave., Miami Beach, Fla. 33141

[21] Appl. No.: 08/825,123

[22] Filed: Mar. 27, 1997

[51] Int. Cl.⁶ .................................................. A61B 5/00
[52] U.S. Cl. ........................................... 600/549; 374/141
[58] Field of Search ................................... 600/549, 474; 374/100, 141, 152

[56] References Cited

U.S. PATENT DOCUMENTS

| | | | |
|---|---|---|---|
| 4,178,916 | 12/1979 | McNamara | 600/549 |
| 4,407,295 | 10/1983 | Steuer et al. | 600/549 |
| 4,509,531 | 4/1985 | Ward | 600/549 |
| 4,747,413 | 5/1988 | Bloch | 600/549 |
| 4,763,112 | 8/1988 | Hsich | 600/549 |
| 4,895,160 | 1/1990 | Reents | 600/549 |
| 5,033,864 | 7/1991 | Lasecki et al. | 600/549 |
| 5,050,612 | 9/1991 | Matsumura | 600/549 |
| 5,464,012 | 11/1995 | Falcone | 600/549 |
| 5,559,497 | 9/1996 | Hong | 600/549 |

Primary Examiner—Cary O'Connor
Assistant Examiner—Charles Marmor, II

[57] ABSTRACT

An infant external temperature monitoring transmitter apparatus with remotely positionable receiver alarm mechanism including an electronic transmitter unit having a temperature sensing mechanism for receiving an external temperature of an infant, a first computing mechanism coupled to the temperature sensor mechanism for providing an indication when the temperature exceeds a preset limit, and a transmitting mechanism coupled to the computing mechanism for transmitting an output signal into free space when the temperature exceeds the preset limit; and an electronic receiver unit having a receiving mechanism for receiving the output signal from the transmitter unit, a second computing mechanism coupled to the receiving mechanism for providing an indication when the output signal exceeds the preset limit, and an alarm mechanism coupled to the second computing mechanism for transmitting an alarm when the indication is received, thereby signifying that the temperature exceeds the preset limit, and for transmitting no alarm otherwise, thereby signifying that the temperature does not exceed the preset limit.

6 Claims, 3 Drawing Sheets

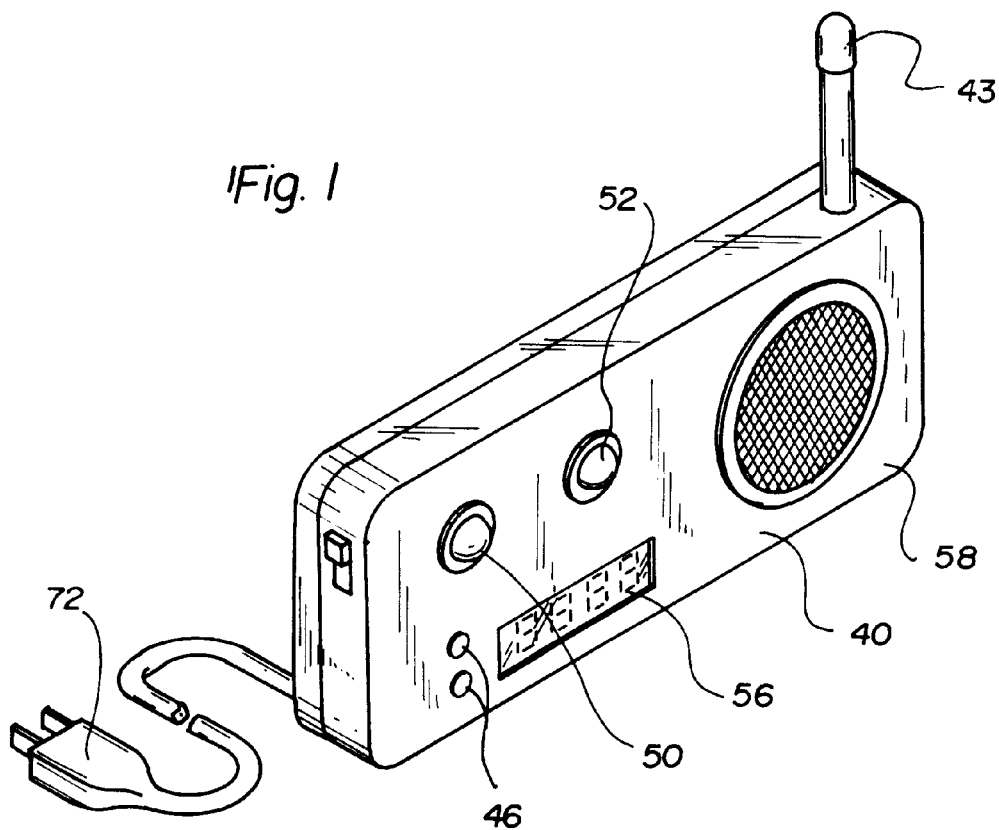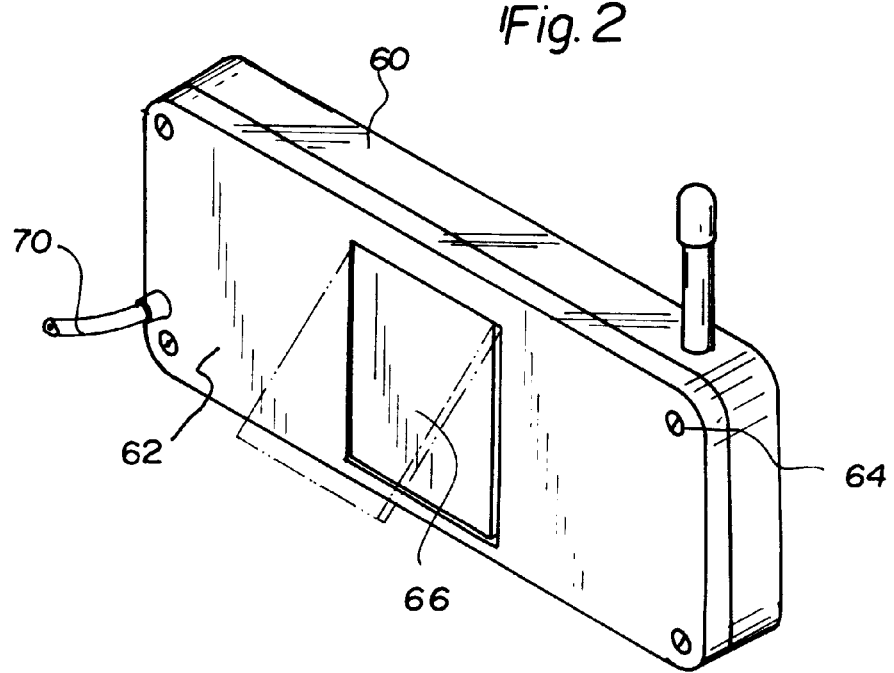

INFANT EXTERNAL TEMPERATURE MONITORING TRANSMITTER APPARATUS WITH REMOTELY POSITIONABLE RECEIVER ALARM MECHANISM

BACKGROUND OF THE INVENTION

1. Field of the Invention

The present invention relates to an infant external temperature monitoring transmitter apparatus with remotely positionable receiver alarm mechanism and more particularly pertains to monitoring the external temperature of an infant and sounding an alarm when the infant's temperature exceeds a preset limit with an infant external temperature monitoring transmitter apparatus with remotely positionable receiver alarm mechanism.

2. Description of the Prior Art

The use of monitoring devices is known in the prior art. More specifically, monitoring devices heretofore devised and utilized for the purpose of monitoring the life functions of individuals are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,488,558 to Simbruner et al. discloses a birth monitor. U.S. Pat. No. 4,747,413 to Bloch discloses an infant temperature measuring apparatus and method. U.S. Pat. No. 4,895,160 to Reents discloses an apparatus for measuring the life functions of a human being, particularly an infant. U.S. Pat. No. 5,010,890 to Pfohl et al. discloses a vital sign monitoring system. U.S. Pat. No. 5,033,864 to Lasecki et al. discloses a temperature sensing pacifier with radio transmitter and receiver. U.S. Pat. No. 5,386,831 to Gluck discloses a remote non-invasive patient temperature monitor and warning system.

While these devices fulfill their respective, particular objective and requirements, the aforementioned patents do not describe an infant external temperature monitoring transmitter apparatus with remotely positionable receiver alarm mechanism that includes a temperature sensor that allows the external body temperature of an infant to be monitored when held thereagainst and a receiver unit that can be positioned in a generally upright orientation through the use of an integral stand.

In this respect, the infant external temperature monitoring transmitter apparatus with remotely positionable receiver alarm mechanism according to the present invention substantially departs from the conventional concepts and designs of the prior art, and in doing so provides an apparatus primarily developed for the purpose of monitoring the external temperature of an infant and sounding an alarm when the infant's temperature exceeds a preset limit.

Therefore, it can be appreciated that there exists a continuing need for new and improved infant external temperature monitoring transmitter apparatus with remotely positionable receiver alarm mechanism which can be used for monitoring the external temperature of an infant and sounding an alarm when the infant's temperature exceeds a preset limit. In this regard, the present invention substantially fulfills this need.

SUMMARY OF THE INVENTION

In the view of the foregoing disadvantages inherent in the known types of monitoring devices now present in the prior art, the present invention provides an improved infant external temperature monitoring transmitter apparatus with remotely positionable receiver alarm mechanism. As such, the general purpose of the present invention, which will be described subsequently in greater detail, is to provide a new and improved infant external temperature monitoring transmitter apparatus with remotely positionable receiver alarm mechanism and method which has all the advantages of the prior art and none of the disadvantages.

To attain this, the present invention essentially comprises, in combination, an electronic transmitter unit. The transmitter unit has a temperature sensing mechanism for receiving an external temperature of an infant. The transmitter unit has a first computing mechanism coupled to the temperature sensor mechanism for providing an indication when the temperature exceeds a preset limit. The transmitter unit has a transmitting mechanism coupled to the computing mechanism for transmitting an output signal into free space when the temperature exceeds the preset limit and a first display mechanism coupled to the first computing mechanism for displaying the temperature. A first housing encases the temperature sensing mechanism, first computing mechanism, and first display mechanism. A coupling mechanism is affixed to the first housing and is securable in a closed-loop configuration for coupling the transmitter unit to an infant.

An electronic receiver unit is also provided. The receiver unit has a receiving mechanism for receiving the output signal from the transmitter unit. The receiver unit has a second computing mechanism coupled to the receiving mechanism for providing an indication when the output signal exceeds the preset limit. A first alarm mechanism is provided and coupled to the second computing mechanism for illuminating a first light source when the indication is received, thereby signifying that the temperature exceeds the preset limit, and for illuminating a second light source otherwise, thereby signifying that the temperature does not exceed the preset limit. The receiver unit includes a second alarm mechanism coupled to the receiving mechanism for generating an audible noise when the indication is received, thereby signifying that the temperature exceeds the preset limit, and for generating no audible noise otherwise, thereby signifying that the temperature does not exceed the preset limit. A second display mechanism is provided and coupled to the second computing mechanism for displaying the temperature. A second housing encases the temperature receiving mechanism, second computing mechanism, and second display mechanism. Lastly, a planar rectangular piece is provided and has an edge hingably coupled to the second housing and positionable at an angle with respect thereto to create a stand for holding the receiver unit in a generally upright orientation.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved infant external temperature monitoring transmitter apparatus with remotely positionable receiver alarm mechanism which has all the advantages of the prior art monitoring devices and none of the disadvantages.

It is another object of the present invention to provide a new and improved infant external temperature monitoring transmitter apparatus with remotely positionable receiver alarm mechanism which may be easily and efficiently manufactured and marketed.

It is a further object of the present invention to provide a new and improved infant external temperature monitoring transmitter apparatus with remotely positionable receiver alarm mechanism which is of durable and reliable construction.

An even further object of the present invention is to provide a new and improved infant external temperature monitoring transmitter apparatus with remotely positionable receiver alarm mechanism which is susceptible of a low cost of manufacture with regard to both materials and labor, and which accordingly is then susceptible of low prices of sale to the consuming public, thereby making such an infant external temperature monitoring transmitter apparatus with remotely positionable receiver alarm mechanism economically available to the buying public.

Still yet another object of the present invention is to provide a new and improved infant external temperature monitoring transmitter apparatus with remotely positionable receiver alarm mechanism which provides in the apparatuses and methods of the prior art some of the advantages thereof, while simultaneously overcoming some of the disadvantages normally associated therewith.

Even still another object of the present invention is to provide a new and improved infant external temperature monitoring transmitter apparatus with remotely positionable receiver alarm mechanism for monitoring the external temperature of an infant and sounding an alarm when the infant's temperature exceeds a preset limit.

Lastly, it is an object of the present invention to provide a new and improved infant external temperature monitoring transmitter apparatus with remotely positionable receiver alarm mechanism comprising an electronic transmitter unit having a temperature sensing mechanism for receiving an external temperature of an infant, a first computing mechanism coupled to the temperature sensor mechanism for providing an indication when the temperature exceeds a preset limit, and a transmitting mechanism coupled to the computing mechanism for transmitting an output signal into free space when the temperature exceeds the preset limit; and an electronic receiver unit having a receiving mechanism for receiving the output signal from the transmitter unit, a second computing mechanism coupled to the receiving mechanism for providing an indication when the output signal exceeds the preset limit, and an alarm mechanism coupled to the second computing mechanism for transmitting an alarm when the indication is received, thereby signifying that the temperature exceeds the preset limit, and for transmitting no alarm otherwise, thereby signifying that the temperature does not exceed the preset limit.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front perspective view of the receiver unit of the present invention.

FIG. 2 is a rear perspective view of the receiver unit of the present invention.

The same reference numerals refer to the same parts through the various Figures.

DESCRIPTION OF THE PREFERRED EMBODIMENT

Figure 3:
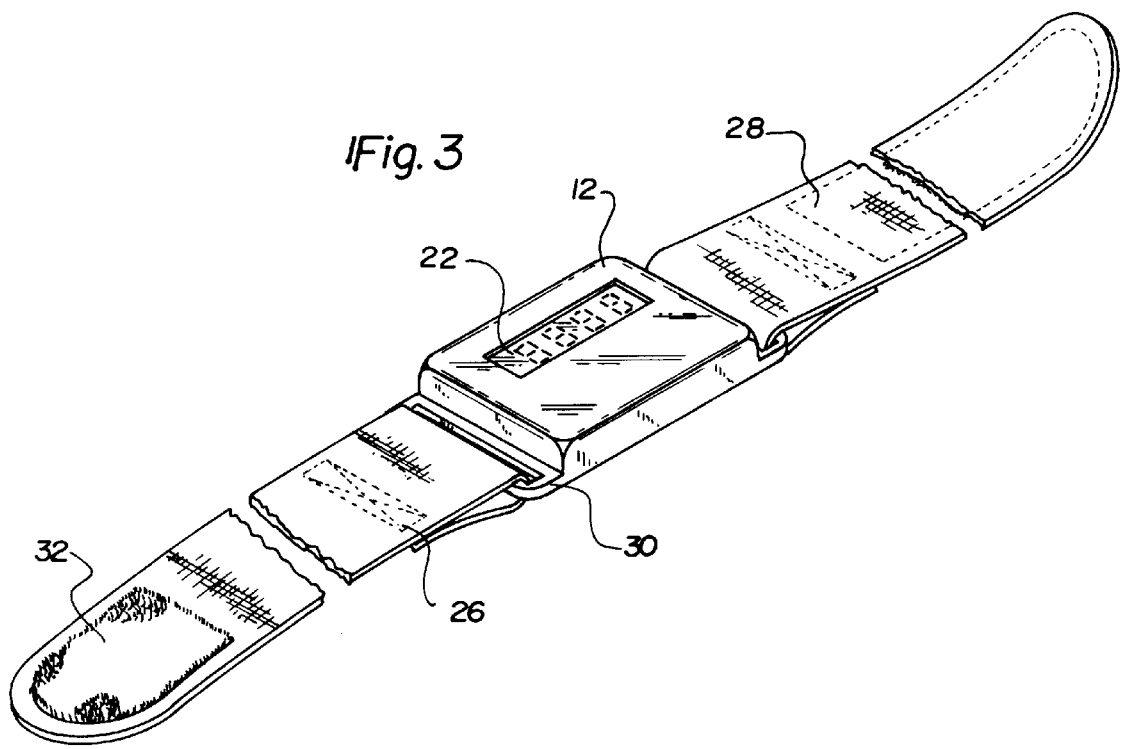
FIG. 3 is a front perspective view of the transmitter unit of the present invention.
Figure 4:
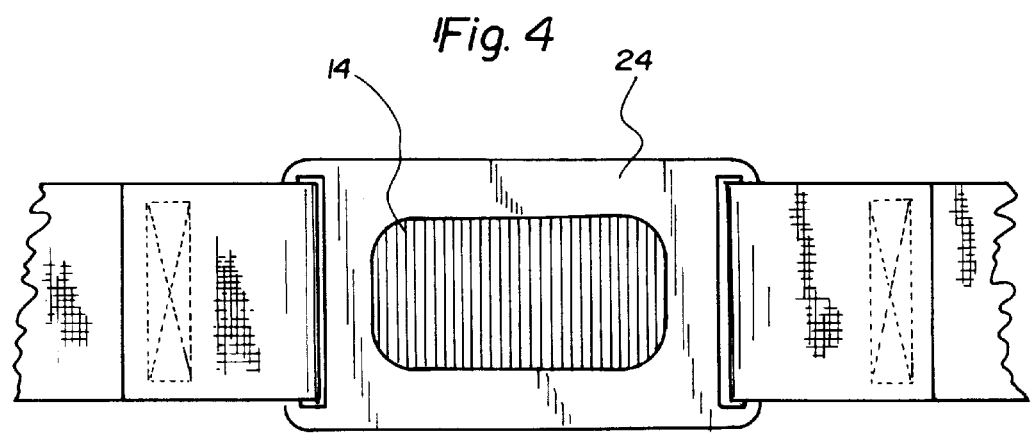
FIG. 4 is an enlarged rear fragmentary view of the transmitter unit of the present invention.
Figure 6:
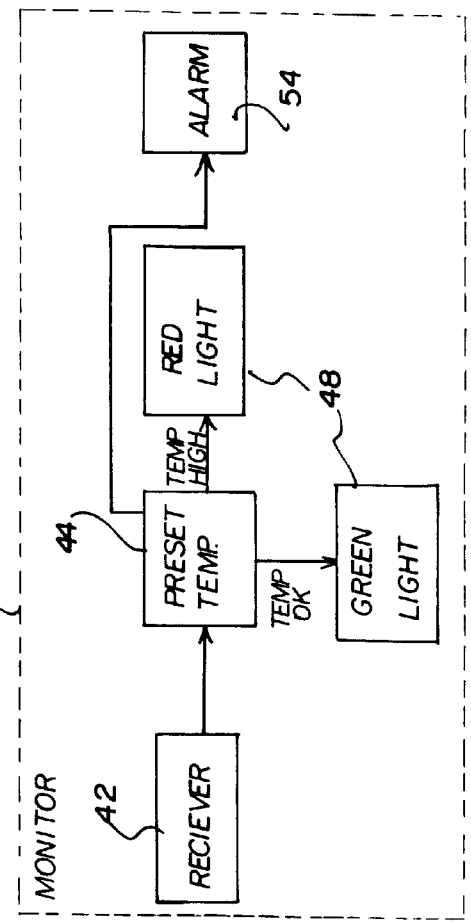
FIG. 6 is a functional block diagram of the receiver unit of the present invention.
Figure 5:
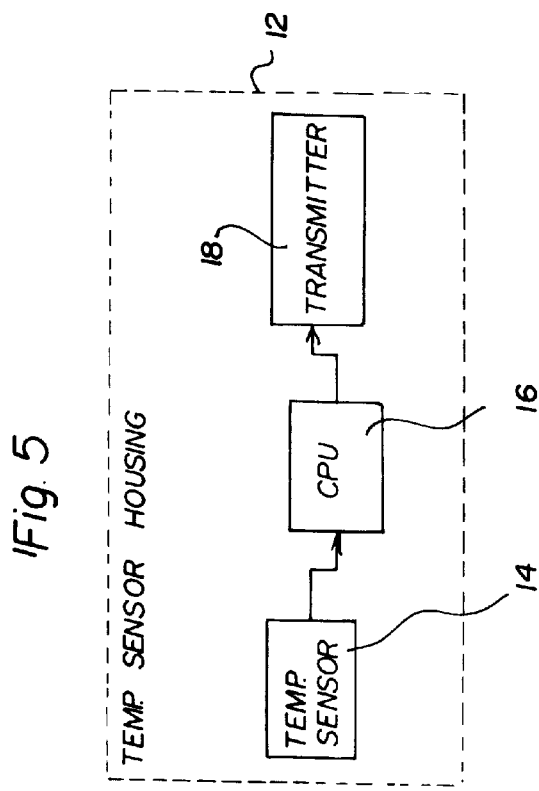
FIG. 5 is a functional block diagram of the transmitter unit of the present invention.

With reference now to the drawings, and in particular, to FIGS. 1 and 3 thereof, the preferred embodiment of the new and improved infant external temperature monitoring transmitter apparatus with remotely positionable receiver alarm mechanism embodying the principles and concepts of the present invention will be described.

The preferred embodiment of the present invention comprises a plurality of components. In their broadest context, such components include a transmitter unit and receiving unit. Such components are individually configured and correlated with respect to each other to provide the intended function of monitoring an infant's external temperature.

Specifically, the present invention includes an electronic transmitter unit 12. The electronic transmitter unit includes a solid state electronic temperature sensing mechanism 14. The temperature sensing mechanism is used for receiving an external temperature such as that of an infant, child, or other person when held thereagainst. The temperature sensing mechanism is conventional in design and commercially available.

The electronic transmitter unit also includes a first computing mechanism 16. The first computing mechanism is connected to the temperature sensor mechanism 14. The first computing mechanism provides an indication when the temperature as received from the temperature sensing mechanism exceeds a preset limit. The preset limit may be adjusted through an unillustrated control dial. The first computing mechanism is conventional in design and is formed of a microprocessor or suitable programmable logic devices.

An electronic transmitter mechanism 18 is also provided and connected to the computing mechanism 16. The transmitting mechanism is conventional in structure and is used for transmitting an output signal into free space through an unillustrated antenna when the temperature exceeds the preset limit as set with the first computing mechanism 16.

A first display mechanism 22 is connected to the first computing mechanism 16. The first display mechanism is preferably formed of a conventional display matrix of light emitting diodes. The first display mechanism is used for displaying the temperature as registered through the first computing mechanism 16.

A first housing 24 formed of a rigid plastic encases the temperature sensing mechanism, first computing mechanism, and first display mechanism. The temperature sensing mechanism 14 extends through the rear of the housing while the first display mechanism 22 extends through the front of the housing. The housing is generally rectangular in shape in the preferred embodiment.

A coupling mechanism 26 is affixed to the first housing 24. The coupling mechanism is formed of a pair of opposed and aligned canvas or leather straps 28. Each strap has an inboard end secured to the housing with a loop 30. Each strap also has an outboard end with a pile-type fastener 32 sewn thereto. The pile-type fasteners are securable in a closed loop configuration for coupling the transmitter directly to an infant's arm or leg. A conventional buckle can also be used in lieu of the pile fasteners. In addition, the straps can be fashioned with a length such that the temperature sensor mechanism 14 can be affixed in a position in direct contact with a person's forehead for monitoring temperature.

The transmitter unit 12 is powered by an unillustrated power source. The power source is formed of a conventional battery. The battery is placed within the housing 24 and removable through an unillustrated access door.

The present invention also includes an electronic receiver unit 40. The receiver unit has a receiving mechanism 42 formed of conventional electronic circuitry for receiving the output signal from the transmitter unit 12 through use of antenna 43. The receiver unit also includes a second computing mechanism 44 that is connected to the receiving mechanism 42. The second computing mechanism provides an indication when the output signal exceeds a preset limit. This preset limit can be the same as that of the transmitter unit or adjusted to a different level through temperature control buttons 46. The second computing mechanism 44 is formed of a conventional microprocessor or with program logic circuitry.

The electronic receiver unit also includes a first alarm mechanism 48. The first alarm mechanism is connected to the second computing mechanism 44. The first alarm mechanism illuminates a first red light-emitting diode 50 when the indication is received, thereby signifying that the temperature exceeds the preset limit. In addition, a second green light-emitting diode 52 is illuminated to signify that the temperature does not exceed the preset limit. A second alarm mechanism 54 is also connected to the receiving mechanism 42 and generates an audible noise when the indication is received, thereby signifying that the temperature exceeds the preset limit. Preferably, the alarm mechanism 54 is formed of a speaker or piezoelectric buzzer. No audible noise is generated if the temperature does not exceed the preset limit. Thus, when an indication of a high temperature is received, both visual and audible signals are provided.

A second display mechanism 56 formed of conventional light-emitting diode circuitry is connected to the second computing mechanism 44. The second display mechanism displays the temperature as registered by the second computing mechanism 44. A second housing 58 encases the temperature receiving mechanism, second computing mechanism, and second display mechanism. The housing 58 is formed of two rigid generally rectangular halves 60, 62 coupled together with screws 64. A grill formed on one of the halves covers the speaker and protects it from being damaged.

A planar rectangular plastic piece 66 or leg is provided. The piece has an edge that is hingably coupled to the second housing 58. The piece is positionable at an angle with respect to the second housing to create a stand. The stand is used for holding the receiver unit in a generally upright orientation.

Electrical power is supplied to the electronic receiver unit 40 through the use of a power cord 70. The power cord has a distal plug end 72. The plug end 72 is removably securable to an external source of electrical power such as a household electrical socket.

The present invention is essentially a wireless battery operated thermometer with receiver alarm. If the transmitter unit is strapped to a sick infant, child, or adult, the receiver unit will sound an alarm when that person's temperature exceeds a preset limit. The present invention can be used around a person's arm or even adjusted to fit across a person's forehead. The present invention can be used in households as well as hospitals. The present invention precludes the need of having another person constantly monitor the temperature of a sick person in order to ensure that his or her temperature does not rise above an established limit.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. An infant external temperature monitoring transmitter apparatus with remotely positionable receiver alarm mechanism comprising, in combination:

an electronic transmitter unit having:
- temperature sensing means for receiving an external temperature of an infant,
- a first computing means in the form of a processing unit coupled to the temperature sensing means for providing an indication when the temperature exceeds a preset limit,
- transmitting means coupled to the computing means for transmitting an output signal into free space when the temperature exceeds the preset limit,
- a first light emitting diode display means coupled to the first computing means for displaying the temperature,
- a first housing encasing the temperature sensing means, first computing means, and first display means,
- coupling means affixed to the first housing and securable in a closed-loop configuration for coupling the transmitter unit to an infant; and an electronic receiver unit having:
- receiving means for receiving the output signal from the transmitter unit,
- second computing means coupled to the receiving means for providing an indication when the output signal exceeds the preset limit,
- first alarm means coupled to the second computing means for illuminating a first light source when the indication is received, thereby signifying that the temperature exceeds the preset limit, and for illuminating a second light source otherwise, thereby signifying that the temperature does not exceed the preset limit,
- second alarm means coupled to the receiving means for generating an audible noise when the indication is received, thereby signifying that the temperature exceeds the preset limit, and for generating no audible noise otherwise, thereby signifying that the temperature does not exceed the preset limit, and
- a second light emitting diode display means coupled to the second computing means for displaying the temperature,
- a second housing encasing the temperature receiving means, second computing means, and second display means, and
- a planar rectangular piece having an edge hingably coupled to the second housing and positionable at an angle with respect thereto to create a stand for holding the receiver unit in a generally upright orientation.

2. An infant external temperature monitoring transmitter apparatus with remotely positionable receiver alarm mechanism comprising:

an electronic transmitter unit having:
- temperature sensing means for receiving an external temperature of an infant,
- a first computing means in the form of a processing unit coupled to the temperature sensing means for providing an indication when the temperature exceeds a preset limit, and
- a first light emitting diode display means coupled to the first computing means for displaying the temperature,
- transmitting means coupled to the computing means for transmitting an output signal into free space when the temperature exceeds the preset limit; and an electronic receiver unit having:
- receiving means for receiving the output signal from the transmitter unit;
- second computing means coupled to the receiving means for providing an indication when the output signal exceeds the preset limit, and
- a second light emitting diode display means coupled to the second computing means for displaying the temperature,
- alarm means coupled to the second computing means for transmitting an alarm when the indication is received, thereby signifying that the temperature exceeds the preset limit, and for transmitting no alarm otherwise, thereby signifying that the temperature does not exceed the preset limit.

3. The infant external temperature monitoring transmitter apparatus with remotely positionable receiver alarm mechanism as set forth in claim 2 wherein the transmitter unit includes coupling means affixed thereto and securable in a closed-loop configuration for coupling the transmitter unit to an infant.

4. The infant external temperature monitoring transmitter apparatus with remotely positionable receiver alarm mechanism as set forth in claim 2 wherein the alarm means of the receiver unit is a visual alarm.

5. The infant external temperature monitoring transmitter apparatus with remotely positionable receiver alarm mechanism as set forth in claim 2 wherein the alarm means of the receiver unit is an audible alarm.

6. The infant external temperature monitoring transmitter apparatus with remotely positionable receiver alarm mechanism as set forth in claim 2 wherein the receiver unit includes a generally planar piece having an edge hingably coupled to the receiver unit and positionable at an angle with respect thereto to create a stand for holding the receiver unit in a generally upright orientation.

* * * * *